US005670487A

United States Patent [19]
Grollier et al.

[11] Patent Number: 5,670,487
[45] Date of Patent: Sep. 23, 1997

[54] COMPOSITION FOR PROTECTING AND/OR COMBATING BLEMISHES ON AND/OR AGEING OF THE SKIN, AND USES THEREOF

[75] Inventors: Jean-Francois Grollier, Paris; Herve Cantin, Morangis; Didier Gagnebien, Chatillon, all of France

[73] Assignee: L'Oreal, Paris, France

[21] Appl. No.: 666,211

[22] Filed: Jun. 20, 1996

[30] Foreign Application Priority Data

Jun. 20, 1995 [FR] France .................................. 95 07335

[51] Int. Cl.⁶ ........................................... A61K 31/70
[52] U.S. Cl. ............................ 514/35; 424/59; 514/25
[58] Field of Search .............................. 424/59; 514/35, 514/25

[56] References Cited

U.S. PATENT DOCUMENTS

| | | | |
|---|---|---|---|
| 4,585,597 | 4/1986 | Lang et al. | 514/510 |
| 4,764,505 | 8/1988 | Fujinuma et la. | 514/35 |

FOREIGN PATENT DOCUMENTS

| | | |
|---|---|---|
| 0 390 682 | 10/1990 | European Pat. Off. . |
| 2 577 805 | 8/1986 | France . |

OTHER PUBLICATIONS

Senoo et al, Chem. Abst., vol. 111, #102,705M (1989).
Tomita et al., Chem. Abst., vol. 113, #197,639w (1990).
Ashara et al, Chem. Abst., vol. 106, #89963u (1987).
Chemical Abstracts, vol. 121, No. 12, Sep. 19, 1994, Abstract No. 141250, A. Yamamoto, "Skin Cosmetics Containing Hydroquinone Glycosides for Preventing UV Damage and Skin Aging."

*Primary Examiner*—James H. Reamer
*Attorney, Agent, or Firm*—Oblon, Spivak, McClelland, Maier & Neustadt, P.C.

[57] ABSTRACT

The invention relates to a composition for combating skin blemishes and/or for combating ageing of the skin, as well as for protecting the skin, particularly against ultraviolet rays. The composition contains arbutin and at least one ultraviolet screening agent chosen from the group consisting of benzylidenecamphor and derivatives thereof, in a cosmetically and/or dermatologically acceptable medium.

28 Claims, No Drawings

COMPOSITION FOR PROTECTING AND/OR COMBATING BLEMISHES ON AND/OR AGEING OF THE SKIN, AND USES THEREOF

BACKGROUND OF THE INVENTION

1. Field of the Invention

The present invention relates to a cosmetic and/or dermatological composition for preventing or combating skin blemishes or ageing of the skin.

The present invention also relates to a cosmetic and/or dermatological composition for protecting the skin, particularly against ultraviolet rays, or for depigmenting the skin. This composition may be applied to the human face, body, legs, hands, or scalp.

The invention also relates to the use of this composition for the cosmetic treatment of the skin, to the use of this composition for the preparation of a cream intended for the dermatological treatment of the skin, and to a cosmetic treatment process.

2. Discussion of the Background

Over time, various signs appear on the skin which are characteristic of ageing. These are reflected in particular by modifications in skin structure and functions. Ageing is physiological in nature but is also photoinduced, i.e., it is due to repeated exposure of the skin to sunlight, in particular ultraviolet light. The action of sunlight or ultraviolet light on the constituents of the skin and on the sebum secreted by the skin results in particular in the formation of oxygen-containing free radicals (hydrophilic chemical radical species such as $O_2^{\bullet -}$ and $OH^{\bullet}$, and lipophilic radical species such as $CH_3^{\bullet}$) which are capable of reacting with skin lipids and forming radicals $ROO^{\bullet}$. These radicals give rise to considerable damage, in particular in cell membranes (permeability of the membranes), cell nuclei (mutation by action on the RNA or DNA), and tissues (necrosis, degeneration). It is thus necessary to protect the skin against these free radicals.

The main clinical signs of ageing of the skin are the appearance of fine lines and deep wrinkles which increase with age, as well as a disorganization of the "grain" of the skin; in other words, the microrelief is less uniform and has an anisotropic nature.

Moreover, the skin complexion is generally modified; it appears paler and yellower. This would appear to be due essentially to a disorganization of the microcirculation (less haemoglobin in the papillary dermis). Furthermore, many age spots, or colored and/or darker blemishes, appear at the surface of the skin, particularly on the hands, giving the skin a heterogeneous appearance. In general, these blemishes are due to a sizeable production of melanin in the skin epidermis or dermis. In certain cases, these blemishes may become cancerous. Moreover, diffuse irritations and sometimes telangiectasia may exist in certain areas of the skin.

Another clinical sign of ageing is rough and dry appearance of the skin, which is due essentially to a higher level of desquamation. By diffracting light rays, these squama also contribute towards a somewhat grey appearance of the complexion.

Finally, loss of skin firmness and tone are noted, which, as for the wrinkles and fine lines, is at least partly explained by dermal and epidermal atrophy as well as by a flattening out of the dermoepidermal formation. The skin is thinner and more flaccid, and the epidermis is of reduced thickness.

Thus, clinical signs of skin ageing result essentially from a dysfunction of the main biological mechanisms involved in the skin.

Many compositions for combating skin blemishes and the signs of ageing and for protecting the skin against the harmful effects of sunlight exist on the market. These compositions are often of insufficient effectiveness.

The most effective active agent to date for combating skin blemishes is hydroquinone. Unfortunately, this compound is very unstable and relatively toxic to the skin, which considerably limits its use. Thus, new compounds or new combinations of compounds have been sought which have a depigmenting and/or protective property, and whose effectiveness is comparable to hydroquinone, but without its drawbacks.

SUMMARY OF THE INVENTION

Accordingly, one object of the present invention is to provide a composition capable of preventing and/or combating the onset of ageing and the signs of ageing, such as wrinkles and fine lines, of preventing or combating pigmentation blemishes on the skin, irrespective of their origin, and of protecting the skin, in particular by suppression of the formation of oxygen-containing free radicals.

Another object of this invention is to provide a novel composition for preventing and/or combating ageing of the skin or skin blemishes, or for protecting the skin, or for depigmenting the skin, having properties which are comparable or even superior to those of compositions based on hydroquinone, but without its drawbacks.

Another object of the invention, according to an essential characteristic thereof, is to provide a composition for topical application containing arbutin and at least one ultraviolet screening agent chosen from the group consisting of benzylidenecamphor and derivatives thereof, in a cosmetically and/or dermatologically acceptable medium, wherein arbutin and screening agent are present in an amount such that their combination shows a synergy of activity against oxygen free radicals. The screening agent is preferably a sulphone-containing and/or sulphonate-containing derivative of benzylidenecamphor.

Another object of this invention is to provide a composition for topical application, wherein it contains, in a cosmetically and/or dermatologically acceptable medium, arbutin and at least one ultraviolet screening agent chosen from the group consisting of sulphone-containing or sulphonate-containing derivatives of benzylidenecamphor.

This and other objects which will become apparent in the course of the following description have been achieved by the composition and method of the present invention.

Surprisingly, Applicants have discovered that the simultaneous use of arbutin and benzylidenecamphor, and/or one of the derivatives thereof, makes it possible to attenuate wrinkles and fine lines, to modify the skin complexion, which appears rosier, to eliminate pigmentation blemishes, to remove squama and to give the skin a more elastic consistency, while at the same time protecting the skin against oxygen free radicals.

Given the relatively low effectiveness of arbutin, it is surprising that benzylidenecamphor and/or derivatives thereof increase quite considerably the effectiveness of arbutin against blemishes and radicals, and increase the protective effectiveness of arbutin, particularly with respect to ultraviolet rays. Since these ultraviolet screening agents have no radical-countering property, it is surprising that their combination with arbutin imparts radical-countering and thus protective properties to the composition. It is also surprising that for determined concentrations, and especially for a concentration from 0.05 to 0.15% by weight of every compound of the combination, the combination of arbutin and screening agent provides synergistic activity against oxygen free radicals.

Synergistic activity or synergism represents the interaction of agents such that the total effect is greater than the sum of the individual effects. Preferably, arbutin and the screening agent are present in amounts such that the increase in effectiveness is at least 3% greater than what one would expect by simple cumulative effect.

Finally, arbutin provides an increase in the protection factor of the UV screening agent. This is quite surprising since arbutin is not at all a screening agent.

FR-A-2577805 describes a composition for treating skin containing a glucosylated derivative of hydroquinone. This composition may contain a screening agent. However, this document does not disclose the specific combination of arbutin and a benzylidenecamphor derivative, and it does not teach that this combination may have notable properties.

Arbutin is a glucosylated derivative of hydroquinone, hydroquinone-beta-D-glucopyranoside, which is generally used as a depigmenting agent. Arbutin is of greater stability than hydroquinone, thereby facilitating its incorporation into supports of all types, and affording them a longer period of use. In addition, arbutin is much less toxic than hydroquinone.

DETAILED DESCRIPTION OF THE PREFERRED EMBODIMENTS

The benzylidenecamphor derivatives which can be used in the invention are preferably sulphone-containing and/or sulphonate-containing derivatives having a wide spectrum of absorption in the UVA (320 nm to 400 nm) and UVB range.

In particular, the benzylidenecamphor derivatives which can be used in the present invention have the following general formula (a):

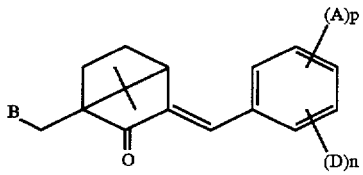

wherein:

B represents —H or —SO$_3$H, $0 \leq p \leq 1$, with the proviso that B=—SO$_3$H when p=0, $0 \leq n \leq 4$, D represents one or more linear or branched alkyl or alkoxy radicals, which may be identical or different when $n \geq 2$, containing from 1 to 18 carbon atoms, a halogen radical or a hydroxyl radical, A, preferably in the meta or para position, represents either an SO$_3$H radical or a group:

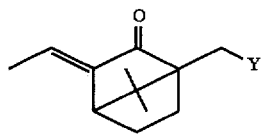

wherein Y represents H or SO$_3$H, or a group:

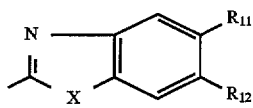

wherein:

R$_{11}$ denotes a hydrogen atom, a linear or branched alkyl or alkoxy radical containing from 1 to 6 carbon atoms, or the —SO$_3$H radical, R$_{11}$ being —SO$_3$H when B=—H, R$_{12}$ denotes a hydrogen atom or a linear or branched alkyl or alkoxy radical containing from 1 to 6 carbon atoms, X is an oxygen or sulphur atom or a group —NR—, R being a hydrogen atom or a linear or branched alkyl radical containing from 1 to 6 carbon atoms, and in which at least one —SO$_3$H function is optionally neutralized.

Neutralization of one or more functions may be obtained using a base generally used in the cosmetics field, such as sodium hydroxide, triethanolamine or potassium hydroxide.

Specific examples of compounds of formula (a) are the derivatives of the following formulae (I), (II) and (III):

Formula (I):

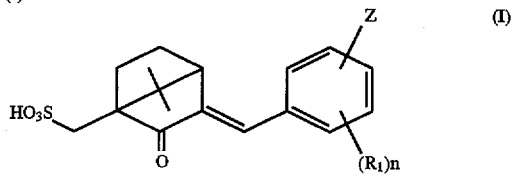

wherein:

Z, preferably in the para or meta position, denotes a group

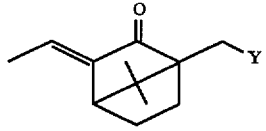

wherein Y represents —H or —SO$_3$H, which is optionally neutralized, n is equal to 0 or is a number ranging from 1 to 4 ($0 \leq n \leq 4$), and R$_1$ represents one or more linear or branched alkyl or alkoxy radicals, which may be identical or different, containing from 1 to 4 carbon atoms.

A particularly preferred compound of formula (I) is that corresponding to n=0, Z in the para position and Y=—SO$_3$H: benzene-1,4-bis(3-methylidenecamphor-10-sulphonic acid), also referred to as terephthalylidene dicamphor sulphonic acid according to the International Cosmetic Ingredient Dictionary, 6th edition, 1995, Cosmetic, Toiletry, and Fragrance Association, Inc. (CTFA).

Formula (II):

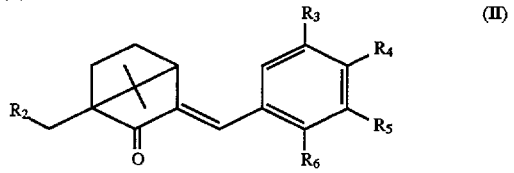

wherein:

R$_2$ denotes a hydrogen atom or an —SO$_3$H radical, and R$_3$, R$_4$, R$_5$ and R$_6$, which may be identical or different, represent a hydroxyl group, a linear or branched alkyl radical having from 1 to 4 carbon atoms, a linear or branched alkenyl radical having from 2 to 4 carbon atoms, a linear or branched alkoxy radical having from 1 to 4 carbon atoms, a linear or branched alkenyloxy radical having from 2 to 4 carbon atoms, or a halo radical; furthermore, a radical $R_3$ to $R_6$ alone may be an —$SO_3H$ radical, at least one of the radicals $R_3$ to $R_6$ is an —$SO_3H$ radical when $R_2$ is a hydrogen atom. One or more —$SO_3H$ functions may also be neutralized.

Specific examples of formula (II) are those in which:

$R_4$ denotes the —$SO_3H$ radical in the position para to the benzylidenecamphor, and $R_2$, $R_3$, $R_5$ and $R_6$ each denote a hydrogen atom, i.e., 3-benzylidenecamphor-4'-sulphonic acid.

$R_3$, $R_4$, $R_5$ and $R_6$ each denote a hydrogen atom and $R_2$ denotes an —$SO_3H$ radical, i.e., 3-benzylidenecamphor-10-sulphonic acid.

$R_4$ denotes a methyl radical in the position para to the benzylidenecamphor, $R_5$ is an —$SO_3H$ radical, and $R_2$, $R_3$ and $R_6$ represent a hydrogen atom, i.e., 3-benzylidenecamphor-4'-methyl-3'-sulphonic acid.

$R_4$ denotes a chlorine atom in the position para to the benzylidenecamphor, $R_5$ is an —$SO_3H$ radical, and $R_2$, $R_3$ and $R_6$ represent a hydrogen atom, i.e., 3-benzylidenecamphor-4'-chloro-3'-sulphonic acid.

$R_4$ denotes a methyl radical in the position para to the benzylidenecamphor, $R_3$, $R_5$ and $R_6$ denote a hydrogen atom, and $R_2$ denotes an —$SO_3H$ radical, i.e., 4,'-methyl-3-benzylidenecamphor-10-sulphonic acid.

$R_2$ represents an —$SO_3H$ radical, $R_3$ is a methyl radical, $R_4$ is a hydrogen atom, $R_5$ is a tert-butyl radical, and $R_6$ is a hydroxyl radical, i.e., 3-(3-t-butyl-2-hydroxy-5-methyl) benzylidenecamphor-10-sulphonic acid.

$R_2$ represents an —$SO_3H$ radical, $R_3$ is a methoxy radical, $R_4$ is a hydrogen atom, $R_5$ is a tert-butyl radical, and $R_6$ is a hydroxyl radical, i.e., 3-(3-t-butyl-2-hydroxy-5-methoxy) benzylidenecamphor-10-sulphonic acid.

$R_2$ represents an —$SO_3H$ radical, $R_3$ and $R_5$ each denote a tert-butyl radical, $R_4$ is a hydroxyl radical, and $R_6$ is a hydrogen atom, i.e., 3-(3,5-di-tert-butyl-4-hydroxy) benzylidenecamphor-10-sulphonic acid.

$R_4$ represents a para-methoxy radical, $R_5$ represents —$SO_3H$, and the radicals $R_2$, $R_3$ and $R_6$ represent H, i.e., 3-benzylidenecamphor-4'-methoxy-3'-sulphonic acid.

$R_2$ denotes an —$SO_3H$ radical, $R_3$ and $R_6$ represent H, and $R_4$ and $R_5$ form a methylenedioxy radical, i.e., 3-(4,5-methylenedioxy)benzylidenecamphor-10-sulphonic acid.

$R_2$ represents an —$SO_3H$ radical, $R_4$ is a methoxy radical and the radicals $R_3$, $R_5$ and $R_6$ are H, i.e., 3-(4-methoxy) benzylidenecamphor-10-sulphonic acid.

$R_2$ represents an —$SO_3H$ radical, $R_4$ and $R_5$ are both a methoxy radical, and the radicals $R_3$ and $R_6$ represent H, i.e., 3-(4,5-dimethoxy)benzylidenecamphor-10-sulphonic acid.

$R_2$ represents an —$SO_3H$ radical, $R_4$ is an n-butoxy radical, and the radicals $R_3$, $R_5$ and $R_6$ represent a hydrogen atom, i.e., 3-(4-n-butoxy)benzylidenecamphor-10-sulphonic acid.

$R_2$ represents an —$SO_3H$ radical, $R_4$ is an n-butoxy radical, $R_5$ is a methoxy radical, and $R_3$ and $R_6$ both denote a hydrogen atom, i.e., 3-(4-n-butoxy-5-methoxy) benzylidenecamphor-10-sulphonic acid.

Formula (III):

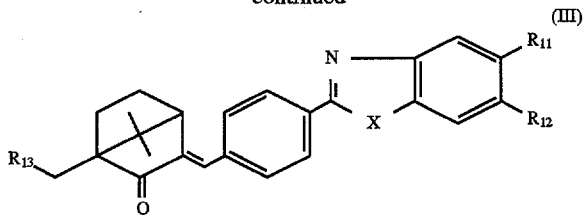

wherein:

$R_{11}$ is a hydrogen atom, a linear or branched alkyl or alkoxy radical containing from 1 to 6 carbon atoms or an —$SO_3H$ radical, $R_{12}$ is a hydrogen atom or a linear or branched alkyl or alkoxy radical containing from 1 to 6 carbon atoms, $R_{13}$ is a hydrogen atom or an —$SO_3H$ radical, wherein at least one of the radicals $R_{11}$ and $R_{13}$ is an —$SO_3H$ radical, and X is an oxygen or sulphur atom or a group —NR—, R being a hydrogen atom or a linear or branched alkyl radical containing from 1 to 6 carbon atoms.

A specific example of a compound of formula (III) is the compound in which X is an —NH— radical, $R_{11}$ is an —$SO_3H$ radical, and $R_{12}$ and $R_{13}$ both denote a hydrogen atom, i.e., 2-[4-(camphormethylidene)phenyl] benzimidazole-5-sulphonic acid.

The compounds of structures (I), (II) and (III) are described in U.S. Pat. No. 4,585,597 and French Patents FR-2,236,515, FR-2,282,426, FR-2,645,148, FR-2,430,938, FR-2,592,380.

Other examples of benzylidenecamphor derivatives which can be used in the present invention are compounds of general formula (b):

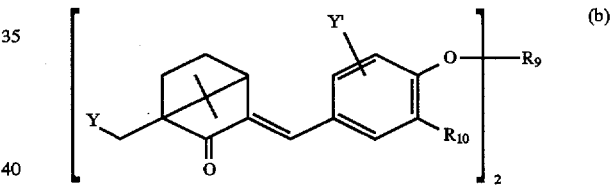

wherein:

$R_9$ is a divalent radical: —$(CH_2)_m$— or —$CH_2$—CHOH—$CH_2$—, m being an integer ranging from 1 to 10 ($1 \leq m \leq 10$), $R_{10}$ is a hydrogen atom, an alkoxy radical containing from 1 to 4 carbon atoms, or a divalent radical —O— connected to the radical $R_9$ when the latter is also divalent, and Y and Y' denote a hydrogen atom or an —$SO_3H$ radical, at least one of these radicals Y or Y' being other than hydrogen. The —$SO_3H$ function may be neutralized.

A specific example of a compound of formula (b) is one in which Y represents —$SO_3H$, Y' is —H, $R_{10}$ is H and $R_9$ is —$CH_2$—$CH_2$—, i.e., ethylenebis[3-(4'-oxybenzylidene) camphor-10-sulphonic acid].

According to the present invention, the amount of arbutin is that conventionally used in the cosmetic or dermatological field. For example, it may be present in a proportion of from 0.05 to 10%, preferably from 0.5 to 5%, more preferably from 1.5 to 3% by weight relative to the total weight of the composition.

Similarly, the amount of UV screening agent which can be used in the invention is that generally used in the fields concerned. In practice, from 0.1 to 10%, preferably from 0.1 to 5%, more preferably from 1 to 3% by weight of screening agent is used relative to the total weight of the composition.

Smaller amounts of each component can also be used. For example, the composition may comprise from 0.05 to 0.15% by weight of arbutin and from 0.05 to 0.15% by weight of the ultraviolet screening agent, relative to the total weight of the composition.

The composition of the invention may be in any pharmaceutical form normally used for topical application, such as solutions, aqueous or aqueous-alcoholic gels, oil-in-water or water-in-oil emulsions, and more particularly droplets of oil dispersed by spherules in an aqueous phase. These spherules may be polymer nanoparticles such as nanospheres and nanocapsules, or preferably lipid vesicles, it being possible for the lipids of these vesicles to be ionic or nonionic. The composition of the invention may be in the form of a cream, an ointment, a lotion or a serum.

The oils which can be used in the invention are those generally used in the fields concerned. They may be plant, mineral or synthetic oils, and possibly silicone-containing and/or fluoro oils.

The amounts of oil and water are those generally used in the fields concerned and depend on the pharmaceutical form of the composition. For an oil-in-water emulsion or a dispersion of oil in water by lipid spherules, the oil may represent from 2 to 40% by weight relative to the total weight of the composition.

The invention may also contain hydrophilic or lipophilic adjuvants such as gelling agents, preserving agents, opacifying agents, emulsifying agents, co-emulsifying agents, neutralizing agents, fragrances and solubilizing or peptizing agents thereof, dyestuffs such as dyes and pigments, and fillers, as well as lipophilic or hydrophilic active agents other than arbutin, benzylidenecamphor and one of the derivatives thereof.

The adjuvants are used in the usual amount and may represent, in total, from 0.1 to 20% by weight. The amount thereof depends on their nature.

The composition of the invention may be applied topically to all parts of the body and face, including the scalp, the legs and the hands.

The invention provides a method using the composition defined above for the cosmetic treatment of wrinkles and/or fine lines on the skin as well as a use of this composition in order to tone, protect, moisturize and/or firm up the skin.

The invention also provides a method using the composition defined above for depigmenting the skin and/or for cosmetically treating skin blemishes due to ageing, these blemishes being present on the face and/or body, including the hands and the scalp, as well as for the preparation of a cream intended for the treatment of skin blemishes of pathological origin.

The invention also provides a method of protecting the skin against free radicals and/or solar rays.

The expression "free radicals" means any radical and/or ionic species of oxygen and of oxygen-containing compounds, including singlet oxygen.

The invention also relates to the use of arbutin as an anti-free-radical active agent in a cosmetic and/or dermatological composition.

The present invention also provides a process for the cosmetic and/or dermatological treatment of the skin, which consists in applying the composition defined above to the skin.

Other features of the invention will become apparent in the course of the following descriptions of exemplary embodiments which are given for illustration of the invention and are not intended to be limiting thereof.

EXAMPLES

The following tests demonstrate the advantages of the present invention. In the examples below, the compositions are given in % by weight, and "qs 100%" means that the ingredient is present in an amount such that the total of all ingredients equals 100%.

Potentiation of the sun protection factor

The aim of the test is to show the ability of the compositions of the invention to protect the skin against UVA by virtue of a high UVA protection factor.

Ten individuals were tested. They were healthy adults of both sexes. An area of skin located on the back of each of the volunteers was subjected to solar exposure after defining the skin type. The exposure was carried out with a UVA spectrum alone (320 nm to 400 nm), supplied by a 150 W xenon lamp fitted with a WG 335 filter 3 mm in thickness and a UG 11 filter 1 mm in thickness. The UV radiation was conducted by 6 liquid, flexible light guides, making it possible to deliver doses of from 6 to 45 joules/cm$^2$ in a 50% geometric progression.

The application was a single dose, in the open air, of $2 \pm 0.02$ µl/cm$^2$, i.e., approximately 0.15 ml of test product per individual, on an area of 75 cm$^2$, measured with a sterile 1 ml Tuberculin syringe graduated to 1/1000 and having a centered cone.

Exposure was approximately 15 min after application of the product. Macroscopic examination of the exposed areas of the skin was performed approximately 2 h after exposure, to evaluate the immediate and permanent pigmentation reactions. The minimum pigmenting dose on the area protected by the product applied (protected MPD) and that on the area in which no product had been applied (non-protected MPD) was performed simultaneously.

The protection factor PF is then calculated as follows:

PF=protected MPD/non-protected MPD

The test was carried out with 3 compositions, each having the same support, containing arbutin, the UV screening agent (terephthalylidene dicamphor sulphonic acid), and the combination of arbutin and the UV screening agent, respectively.

The UVA sun protection factors are indicated in the following table:

| Composition | UVA sun protection factor |
| --- | --- |
| with 5% arbutin | 1.6 |
| with 1% terephthalylidene dicamphor sulphonic acid | 2.7 |
| with 5% arbutin and 1% terephthalylidene dicamphor sulphonic acid | 3.4 |

These results show a potentiation of the UVA sun protection factor when arbutin is added to the filter. The sun protection factor of 1.6 for arbutin alone represents negligible skin protection. The sun protection factor of 2.7 for the screening agent alone represents significant skin protection. As is well known to one skilled in the art, sun protection factors are not additive, and are very difficult to increase. Thus, in UVA, the change observed from a protection factor of 2.7 with the screening agent alone to a protection factor of 3.4 for the combination of screening agent and arbutin represents significantive potentiation.

Demonstration of Synergism of Anti-free-radical Activity: Arbutin and Benzylidene Camphor Sulphonate Derivative Anti-free-radical activity was demonstrated by a test of inhibition of the production of ethylene. The following were introduced in order into a Petri dish 32 mm in diameter:

1.4 ml of 50 mM phosphate buffer (pH=7.4),
100 µl of 200 mM methionine solution
100 µl of 4 mM ferric chloride solution, 100 µl of test product, 100 µl of 4 mM EDTA (ethylenediaminetetraacetic acid) solution, 100 µl of 400 mM NADH (nicotinamideadeninedinucleotide, reduced form) solution, 100 µl of 2 mM riboflavin solution.

Total volume of the mixture: 2 ml.

The Petri dish was then placed in an aluminum crucible and covered with a quartz cell so as to be exposed to UVA rays (365 nm) at a dose of 1 J/cm$^2$. The mixture, composed of NADH, riboflavin, ferric chloride and EDTA, when subjected to exposure to the UVA rays, generates reduced oxygen species: $O_2^{\bullet-}$, $H_2O_2$, and mainly the hydroxyl radical •OH. The latter reacts with methionine to release ethylene. The amount of ethylene was measured by gas chromatography.

The smaller the amount of free radicals formed, the smaller the amount of ethylene released. The results are expressed as a percentage of inhibitory power corresponding to the percentage decrease in the production of ethylene relative to the control (containing 100 µl of phosphate buffer replacing the test product).

The following substances studied were introduced using a micropipette:

arbutin terephthalylidene dicamphor sulphonic acid

Chromatographic conditions (Varian 3740 type machine)
injector temperature: 80° C.,
column temperature: 80° C.,
detector temperature: 250° C.,
helium pressure: 36 psi (i.e., about 2.4×10$^5$ Pa),
column: F1 alumina 60/80 mesh (source: Supelco),
length: 2 m,
outside diameter: ⅛.

The results (average of 3 tests) are summarized in the following table:

| Sample | % inhibition |
| --- | --- |
| 0.2% arbutin | 39.0 ± 0.6 |
| 0.2% terephthalylidene dicamphor sulphonic acid | 44.7 ± 1.7 |
| 0.1% arbutin + 0.1% terephthalylidene dicamphor sulphonic acid | 52.8 ± 1.5 |

These results show the synergism of anti-free-radical activity of the combination according to the invention.

EXAMPLE 1

Water-in-oil cream for protection of the skin against UVA rays and/or prevention of pigmentation of the skin
Composition

| | | |
| --- | --- | --- |
| A$_1$ | Sorbitan tristearate (emulsifying agent) | 0.9% |
| | Polyethylene glycol stearate (40 EO) (emulsifying agent) | 2.0% |
| | Cetyl alcohol of natural origin (co-emulsifying agent) | 4.0% |
| | Glyceryl mono-, di-, tri-palmitostearate (emulsifying agent) | 3.0% |
| | Myristyl myristate (oil) | 2.0% |
| | 2-Ethylhexyl palmitate (oil) | 5.0% |
| | Hydrogenated isoparaffin (6–8 mol of isobutylene) (oil) | 6.5% |
| A$_2$ | Cyclopentadimethylsiloxane (oil) | 5.0% |

-continued

| | | |
| --- | --- | --- |
| B | Sterilized demineralized water qs | 100% |
| | Glycerol (moisturizing agent) | 3.0% |
| | Arbutin | 5.0% |
| | Denatured absolute ethyl alcohol | 10.0% |
| | Methyl para-hydroxybenzoate (preserving agent) | 0.2% |
| C | Terephthalylidene dicamphor sulphonic acid at a concentration of 33% in water | 3.33% |
| | Triethanolamine (neutralizing agent) | 0.67% |

Preparation of the phase A$_1$+A$_2$

The constituents of A$_1$ were solubilized at 80° C. When the mixture was clear, the temperature was lowered to 65° C. and A$_2$ was added. The mixture must be clear and homogeneous. The temperature of 65° C. was maintained.

Procedure

The constituents of B were solubilized at 85° C.–90° C. in a manufacturing beaker. After verifying that the mixture was clear, the temperature was lowered to 65° C. The emulsion was prepared, with stirring, by pouring (A$_1$+A$_2$) into B. Cooling was continued with stirring. Phase C was added at 40° C. while stirring, and the mixture was left to cool to 20° C. while stirring.

Compositions 2, 3 and 4 were prepared in the same way.

EXAMPLE 2

Oil-in-water cream for combating blemishes
Composition

| | | |
| --- | --- | --- |
| A$_1$ | Demineralized water | 10.0% |
| | Cholesterol | 1.5% |
| | Polyethylene glycol monostearate | 1.5% |
| | Monosodium salt of n-(stearic acid) of α-glutamic acid (vesicles) | 0.2% |
| A$_2$ | Demineralized water | 13.0% |
| | Glycerol (moisturizing agent) | 3.0% |
| | Phenoxyethanol (preserving agent) | 0.7% |
| B | Apricot kernel oil | 9.0% |
| | Refined soya oil | 4.0% |
| | Cyclopentadimethylsiloxane (oil) | 10.0% |
| | Propyl para-hydroxybenzoate | 0.1% |
| | Fragrance | 0.3% |
| C | Carboxyvinyl polymer synthesized in methylene chloride (gelling agent) | 0.7% |
| | Demineralized water qs | 100% |
| | Triethanolamine (neutralizing agent) | 0.7% |
| D | Demineralized water | 5% |
| | Arbutin | 1% |
| E | Terephthalylidene dicamphor sulphonic acid at a concentration of 33% in water | 2.3% |
| | Triethanolamine | 0.6% |

Procedure

The constituents of A$_1$ were melted at 100° C. The mixture was left to swell for 1 h 30 min with stirring. When the mixture was homogeneous, A$_2$ was added; the temperature was stabilized at 80° C. The mixture was then passed twice through a high-pressure homogenizer in order to form the vesicles. B was prepared at 70° C.; the mixture must be clear. It was cooled to 50° C. B was added to A at 50° C.

The mixture was then passed twice through the high-pressure homogenizer in order to disperse the fatty phase B. The mixture was cooled to 30° C. C was added (the gel was prepared beforehand in water at 80° C., by powdering in the carboxyvinyl polymer; after the latter had swollen, it was neutralized using triethanolamine, with stirring; the gel must be quite smooth). D was added, followed by E. The stirring was continued for 5 minutes, completing the manufacture.

EXAMPLE 3

Gel for protecting against solar rays
Composition

| A | Demineralized water qs | 100% |
|---|---|---|
|   | Carboxyvinyl polymer | 0.45% |
|   | Triethanolamine | 0.45% |
| B | Demineralized water | 59.8% |
|   | Glycerol | 3% |
|   | Methyl para-hydroxybenzoate | 0.2% |
|   | Arbutin | 1% |
|   | Xanthan gum (gelling agent) | 0.2% |
| C | Terephthalylidene dicamphor sulphonic acid at a concentration of 33% in water | 2.3% |
|   | Triethanolamine | 0.6% |

Procedure

The gel (carboxyvinyl polymer) was prepared as in Example 2, in water at 80° C. After solubilization of the constituents of B at 80° C., B was added to A. The mixture was made smooth and left to cool with slow paddle stirring. C was added at 35° C. The mixture was left to cool to 25° C., completing the manufacture of the gel.

EXAMPLE 4

"Clear complexion" lotion
Composition

| A | Oxyethylenated hydrogenated ricinoleic triglycerides (60 EO) (septizing agent) | 0.09% |
|---|---|---|
|   | Fragrance | 0.03% |
| B | Demineralized water qs | 100% |
|   | Glycerol | 5.5% |
|   | Arbutin | 1% |
|   | Citric acid | 1% |
|   | 99% triethanolamine | 1.9% |
|   | Imidazolidinylurea (preserving agent) | 0.3% |
| C | Terephthalylidene dicamphor sulphonic acid at a concentration of 33% in water | 2.3% |
|   | Triethanolamine | 0.6% |

Procedure

The constituents of A were mixed together at 40° C. When they were fully solubilized, the constituents of B were successively added at room temperature. Stirring was continued and the constituents were checked to make sure that they had solubilized correctly. C was added; the mixture must be clear. The manufacture was complete.

This application is based on French Patent Application No. 95-07335, filed on Jun. 20, 1995, which is incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by letters patent of the United States is:

1. A composition comprising:
   a) arbutin; and
   b) an ultraviolet screening agent selected from the group consisting of benzylidenecamphor and a benzylidenecamphor derivative, wherein arbutin and the screening agent are present in amounts such that their combination shows a synergy of activity against oxygen free radicals.

2. The composition of claim 1, wherein the screening agent is a sulphone-containing or sulphonate-containing benzylidenecamphor derivative.

3. The composition of claim 1, wherein the screening agent comprises a benzylidenecamphor derivative which has the following formula (I):

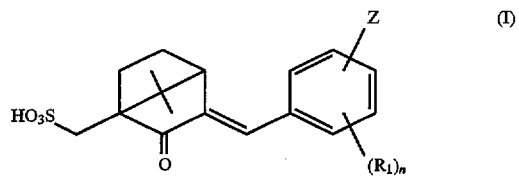

wherein Z is:

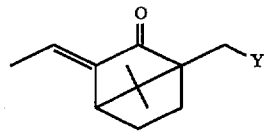

wherein Y represents —H, —SO$_3$H, or neutralized —SO$_3$H, n is equal to 0 or is a number ranging from 1 to 4 ($0 \leq n \leq 4$), and R$_1$ represents one or more linear or branched alkyl or alkoxy radicals, which may be identical or different, containing from 1 to 4 carbon atoms.

4. The composition of claim 1, comprising the benzylidenecamphor derivative terephthalylidene dicamphor sulphonic acid.

5. The composition of claim 1, wherein the composition is in the form of an emulsion, a gel, or a dispersion of spherules.

6. The composition of claim 1, wherein arbutin represents from 0.05 to 10% by weight relative to the total weight of the composition.

7. The composition of claim 1, wherein the ultraviolet screening agent represents from 0.1 to 10% by weight relative to the total weight of the composition.

8. The composition of claim 1, comprising from 0.05 to 0.15% by weight of arbutin and from 0.05 to 0.15% by weight of the ultraviolet screening agent, relative to the total weight of the composition.

9. The composition of claim 1, further comprising a hydrophilic or lipophilic adjuvant.

10. The composition of claim 9, wherein the adjuvant is one selected from the group consisting of gelling agents, preserving agents, fragrances, fillers, dyestuffs, and active agents other than arbutin and said ultraviolet screening agent.

11. A method of cosmetically or dermatologically depigmenting or beautifying skin, comprising applying a depigmenting or beautifying amount of a composition comprising:
   a) arbutin; and
   b) an ultraviolet screening agent selected from the group consisting of benzylidenecamphor and a benzylidenecamphor derivative to the skin of a human being.

12. A method of protecting skin against free radicals and/or solar rays, comprising applying an effective amount to protect the skin against free radicals and/or solar rays of a composition of comprising:

a) arbutin: and b) an ultraviolet screening agent selected from the group consisting of benzylidenecamphor and a benzylidenecamphor derivative to the skin of a human being.

13. The method of claim 11 wherein the composition is applied to wrinkles or fine lines on the skin.

14. The method of claim 11 wherein the composition is applied to skin lacking tone or lacking firmness.

15. The method of claim 11 wherein the composition is applied to skin blemishes.

16. The method of claim 11 wherein the composition is applied to age spots.

17. The method of claim 11 wherein the composition is in the form of a cream.

18. The composition of claim 1, wherein the screening agent comprises benzylidenecamphor.

19. The composition of claim 1, wherein the composition is in the form of a cream.

20. The composition of claim 1, wherein said arbutin and said ultraviolet screening agent each are present in an amount such that their combination shows at least a 3% greater effectiveness against oxygen free radicals than would be expected based upon their cumulative effect.

21. The composition of claim 1, wherein said composition comprises a benzylidenecamphor derivative which is a benzylidenecamphor sulfonic acid compound.

22. The composition of claim 1, wherein said composition comprises a benzylidenecamphor derivative of the general formula (a):

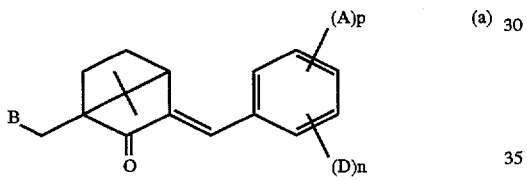

wherein:

B represents —H or —SO$_3$H,

0≦p≦1, with the proviso that B=—SO$_3$H when p=0,

0≦n≦4,

D represents one or more linear or branched alkyl or alkoxy radicals, which may be identical or different when n≧2, containing from 1 to 18 carbon atoms, a halogen radical or a hydroxyl radical, A represents either an SO$_3$H radical or a group:

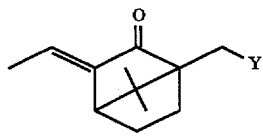

wherein Y represents H or SO$_3$H, or a group:

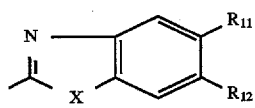

wherein:

R$_{11}$ denotes a hydrogen atom, a linear or branched alkyl or alkoxy radical containing from 1 to 6 carbon atoms, or an —SO$_3$H radical, R$_{11}$ being —SO$_3$H when B=—H, R$_{12}$ denotes a hydrogen atom or a linear or branched alkyl or alkoxy radical containing from 1 to 6 carbon atoms, X is an oxygen or sulphur atom or a group —NR—, R being a hydrogen atom or a linear or branched alkyl radical containing from 1 to 6 carbon atoms, wherein at least one —SO$_3$H function is optionally neutralized.

23. The composition of claim 1, wherein said composition comprises a benzylidenecamphor derivative of the formula (II):

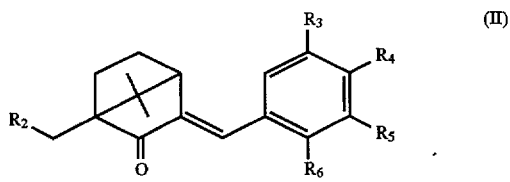

wherein:

R$_2$ denotes a hydrogen atom or an —SO$_3$H radical, and

R$_3$, R$_4$, R$_5$ and R$_6$, which may be identical or different, represent a hydroxyl group, a linear or branched alkyl radical having from 1 to 4 carbon atoms, a linear or branched alkenyl radical having from 2 to 4 carbon atoms, a linear or branched alkoxy radical having from 1 to 4 carbon atoms, a linear or branched alkenyloxy radical having from 2 to 4 carbon atoms, or a halo radical; furthermore, a radical R$_3$ to R$_6$ alone may be an —SO$_3$H radical, and at least one of the radicals R$_3$ to R$_6$ is an —SO$_3$H radical when R$_2$ is a hydrogen atom, wherein at least one —SO$_3$H function is optionally neutralized.

24. The composition as claimed in claim 1, wherein said ultraviolet screening agent comprises a benzylidenecamphor derviative which is selected from the group consisting of:

3-benzylidenecamphor-4'-sulphonic acid;

3-benzylidenecamphor-10-sulphonic acid;

3-benzylidenecamphor-4'-methyl-3'-sulphonic acid;

3-benzylidenecamphor-4'-chloro-3'-sulphonic acid;

4'-methyl-3-benzylidenecamphor-10-sulphonic acid;

3-(3-t-butyl-2-hydroxy-5-methyl)benzylidenecamphor-10-sulphonic acid;

3-(3-t-butyl-2-hydroxy-5-methoxy)benzylidenecamphor-10-sulphonic acid;

3-(3,5-di-tert-butyl-4-hydroxy)benzylidenecamphor-10-sulphonic acid;

3-benzylidenecamphor-4'-methoxy-3'-sulphonic acid;

3-(4,5-methylenedioxy)benzylidenecamphor-10-sulphonic acid;

3-(4-methoxy)benzylidenecamphor-10-sulphonic acid;

3-(4,5-dimethoxy)benzylidenecamphor-10-sulphonic acid;

3-(4-n-butoxy)benzylidenecamphor-10-sulphonic acid; and 3-(4-n-butoxy-5-methoxy)benzylidenecamphor-10-sulphonic acid.

25. The composition as claimed in claim 1, wherein said composition comprises a benzylidenecamphor derivative of the formula III:

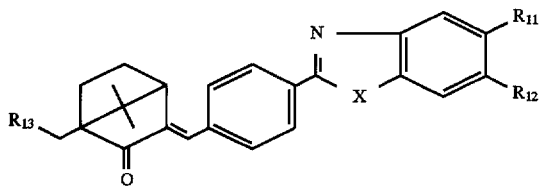

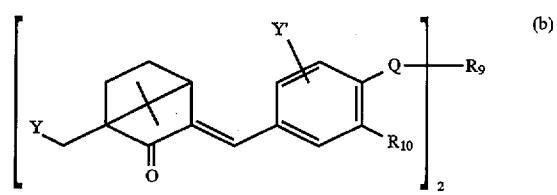

wherein:

R₁₁ is a hydrogen atom, a linear or branched alkyl or alkoxy radical containing from 1 to 6 carbon atoms or an —SO₃H radical, R₁₂ is a hydrogen atom or a linear or branched alkyl or alkoxy radical containing from 1 to 6 carbon atoms, R₁₃ is a hydrogen atom or an —SO₃H radical, wherein at least one of the radicals R₁₁ and R₁₃ is an —SO₃H radical, and X is an oxygen or sulphur atom or a group —NR—, R being a hydrogen atom or a linear or branched alkyl radical containing from 1 to 6 carbon atoms.

26. The composition as claimed in claim 25, wherein said compound of formula III is 2-[4-(camphormethylidene)phenyl]benzimidazole-5-sulfonic acid.

27. The composition as claimed in claim 1, wherein said composition comprises a benzylidenecamphor derviative of formula (b):

wherein:

R₉ is a diavlent radical: —(CH₂)ₘ— or —CH₂—CHOH—CH₂—, m being an integer ranging from 1 to 10 (1≦m≦10), R₁₀ is a hydrogen atom, an alkoxy radical containing from 1 to 4 carbon atoms, or a divalent radical —O— connected to the radical R₉ when the latter is also divalent, and Y and Y' denote a hydrogen atom or an —SO₃H radical, at least one of these radicals Y or Y' being other than hydrogen, wherein the —SO₃H function may be neutralized.

28. The composition as claimed in claim 27, wherein said compound of formula (b) is ethylenebis[3-(4'-oxybenzylidene)camphor-10- sulfonic acid].

* * * * *